(12) United States Patent
Chauhan et al.

(10) Patent No.: US 6,989,160 B2
(45) Date of Patent: Jan. 24, 2006

(54) THERAPEUTIC/EDIBLE COMPOSITIONS COMPRISING HERBAL INGREDIENTS AND METHODS FOR TREATING HYPERGLYCEMIA

(75) Inventors: Abhay Singh Chauhan, Andhra Pradesh (IN); Kishore Babu Chalasani, Andhra Pradesh (IN); Sridevi Surapanini, Andhra Pradesh (IN); Sharath Kumar Yandrapu, Andhra Pradesh (IN); Rajasekhar Kataram, Andhra Pradesh (IN); Govardhana Maroju Chary, Andhra Pradesh (IN); Prakash Vamanrao Diwan, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/101,501

(22) Filed: Mar. 19, 2002

(65) Prior Publication Data
US 2003/0180399 A1 Sep. 25, 2003

(51) Int. Cl.
*A61K 35/78* (2006.01)

(52) U.S. Cl. ............ 424/725; 424/735; 424/761; 424/766; 424/774; 424/777

(58) Field of Classification Search ........... 424/725, 424/735, 761, 766, 774, 777
See application file for complete search history.

(56) References Cited

U.S. PATENT DOCUMENTS 5,886,029 A * 3/1999 Dhaliwal

FOREIGN PATENT DOCUMENTS

DE 4330597 A1 * 3/1995
DE 19720761 A1 * 11/1998

OTHER PUBLICATIONS

Rai et al. (Plant Foods for Human Nutrition (1997), vol. 50, No. 1, pp. 9-16).*
Teotia et al. (Indian Journal of Experimental Biology (1997), vol. 35, No. 3, pp. 295-296).*

* cited by examiner

*Primary Examiner*—Susan D. Coe
(74) *Attorney, Agent, or Firm*—Ladas and Parry LLP

(57) ABSTRACT

A therapeutic or an edible composition comprising at least three of the five herbs selected from *Prunus amygdales, Ocimum sanctum, Azadirachta indica, Aegle marelose* and *Vitus vinefera,* is provided for the treatment of hyperglycemia, especially for non-insulin dependent diabetic subjects, and the herbal composition has significantly reduced the blood glucose levels in both diabetic and non-diabetic experimental subjects having elevated blood glucose levels.

9 Claims, 1 Drawing Sheet

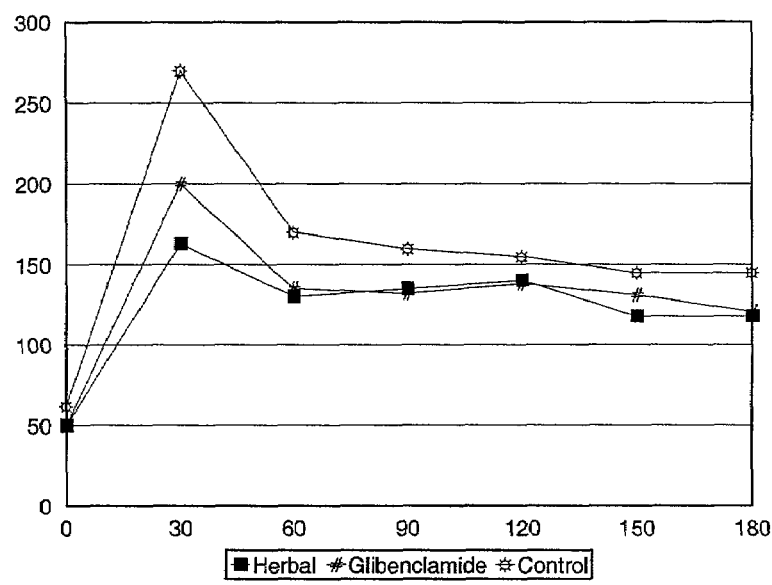
Figure-1. Effect of herbal formulation and glibenclamide on oral glucose tolerance test in rats. No. of rats =6, P<0.05

THERAPEUTIC/EDIBLE COMPOSITIONS COMPRISING HERBAL INGREDIENTS AND METHODS FOR TREATING HYPERGLYCEMIA

FIELD OF THE INVENTION

The present invention relates to an edible or medicinal herbal composition consisting of five different herbs and use of as hypoglycemic agent for lowering the blood glucose levels in mammals, especially humans, suffering from diabetic mellitus.

BACKGROUND OF THE INVENTION

Diabetes mellitus is an insidious medical condition for which there is no permanent cure. Across the globe many humans are suffering with this disease and with its implications such as heart attacks, strokes, loss of eyesight, difficulty in wound healing, more susceptible to disorders of aging and such conditions worsening to death. The onset of diabetes can occur in early age of life although many people are getting in much later part of life.

The medical condition of diabetes characterized by the inability of the pancreas gland to secrete "insulin". Insulin is produced in the body by the beta cells of pancreas gland and helps in the metabolism of glucose to produce the energy required by the humans. In the diabetic patients the pancreas gland deteriorates and the beta cells are too small and insufficiently numerous to produce a proper amount of insulin. Hence the sugar is not properly metabolized to produce energy. As a result, diabetic patient experience an elevated levels of sugar in the blood. The diabetes can be broadly categorized into IDDM and NIDDM. Roughly "IDDM" refers to insulin dependent diabetes mellitus or type I wherein, anti-bodies destroy β-cells of islets of Langerhans which produce insulin and hence very low and no insulin levels in the circulation. In NIDDM there is no loss or moderate reduction in β-cell mass and is due to abnormality in gluco-receptor of β-cells, reduced sensitivity of peripheral tissues to insulin.

The conventional treatment of IDDM involves the administration of insulin to a patient typically by means of injections. These injections must be performed on a regular basis and are normally administered by an hypodermic needle. This is inconvenient to a patient since the administration of insulin using hypodermic needle requires both a suitable place and time to perform the injection, apart from a great deal discomfort to the patient. Also, if the amount of insulin is excessive for amount of sugar in the blood, the patient can undergo insulin shock. If a patient is unwilling or not able to accept insulin injections, pharmaceutical preparations containing oral anti-diabetic drugs such as sulfonylureas (Glibinclamide, Gliquidone etc.) or biguanides (metformin, phenformin) or insulin sensitizers such as troglitozones could be taken. All in all, the patient is constantly on the narrow edge of either too much or insufficient medication and frequently is not able to tolerate such medication because of its side effects.

To control proper blood sugar levels there by controlling this dysfunction so as prevent eventual complications, insulin independent diabetics must maintain a regulated diet control and exercise. Unfortunately most of the diabetics experience to great of difficulty to follow such restrictions leading to worsening of associated complications. Further more, treating with insulin never cures this disorder and there is an urgent need to treat this disease with natural products, which have the advantages of patient compliance and least side effects compared to synthetic medicines. The usage of herbs in the treatment of medical ailments has been a tradition in many countries like India, china etc for so many years, and several diseases can be cured without any side effects.

Hypoglycemic efficacy of different parts of *Azadirachta indica* was evaluated by different researchers (Sonia & Srinivas, 1999, Santoshkumari and Devi, 1990, Murty et.al., 1978, Dixit et.al., 1986, Shukla et.al., 1973, Jain,1984). Hypoglycemic effects of (–)-epicatchin (Chakravarthy et. al. 1982), *Gymnesma sylvestre* (Asha et. al. 1981), *Trigonella foenum graecum* (Khosla et. al. 1995) have been reported. Herbal composition containing different compositions of *Trigonella foenum graecum, Nigella sativa, Orgnanum vulgare, Rosmarinus officinalis, Lupinusterms, Lawsonia inermis* and *Foemiculum vulgare* and methods to treat diabetes mellitus were described in U.S. Pat. No. 6,042,834 (Baraka, 2000). Hypoglycemic extracts for treating diabetes which were obtained from different species of genus Eugena of myrtaceae family were disclosed in US PTO Pub. No. US 2001/0021401 A1 (Sharma et.al. 2001). Similarly medicinal compositions, described as pancreas tonic, containing Epicatechin (pterocarpus marsupium), gymnemic acid (gymnema sylvestre) along with other plant products such as *Cinnamomum tamala, Momardica charantia, Aegle marelose, Syzygium cumini, Trigunella foenum graceum* and *Azadirachta indica, Tinospora cordifolia, Ficus racemosa* was described in U.S. Pat. No. 5,886,029 (Dhaliwal, 1999). A different herbal edible composition containing *Syzygim cumini, Gymne sylvestre, Momordica charantia* and *Solanum melogena* was described in U.S. Pat. No. 5,900,240 (Tomer et.al. 1999).

OBJECTS OF THE INVENTION

The main object of the present invention is to provide a herbal composition of medicinal or edible nature to treat diabetic patients for controlling diabetes mellitus without any side effects.

Another object is to provide a herbal composition which is inexpensive and easily digestible.

SUMMARY OF THE INVENTION

The invention provides an edible therapeutic herbal composition useful as a hypoglycemic agent, comprising a mixture of at least three herbs selected from the group consisting *Prunus amygdales, Ocimum sanctum, Azadirachta indica, Aegle marelose* and *Vitus vinefera,* in therapeutically effective amounts.

In an embodiment, the herbal composition comprises 15–40% w/w of each of the three herbs.

In another embodiment, the composition is formulated as oral dosage forms comprising solutions, suspensions, emulsions, gels, pastes, elixirs, viscous colloidal dispersions, tablets, capsules and/or oral control release types or such delivery forms suitable for oral route.

In still another embodiment, the herbs are selected from dried fruits of *Prunus amygdalus,* leaves of *Ocimum santum,* leaves of *Azaidarchta indica,* leaves of *Agilo marelose* and fruits of *Vitus vinefera.*

In another embodiment, the invention provides a method of treatment for hyperglycemia in humans and animals, comprising the step of oral administration of herbal composition comprising a mixture of at least three herbs selected from the group consisting *Prunus amygdales, Ocimum sanc-* tum, *Azadirachta indica, Aegle marelose* and *Vitus vinefera*, in therapeutically effective amounts.

In yet another embodiment, the herbal composition is administered before food.

In another embodiment, the herbal composition may be administered along with diet of the patient.

In still another embodiment, the composition is administered in a dosage form containing 0.01–0.5 gm/Kg. of the composition.

In another embodiment, the invention provides a method for reducing the blood glucose level in a mammal which comprises of a therapeutically effective amount of the composition of the invention.

DETAILED DESCRIPTION OF THE INVENTION

The present invention provides a composition consisting of five different herbs for treatment and controlling diabetes mellitus, more particularly to non-insulin dependent diabetics. This herbal composition consists of *Prunus amygdales, Ocimum sanctum, Azadirachta indica, Aegle marelose* and *Vitus vinefera*. These plants may be found in various places in the world. The composition containing mixture (Composition F1 in Table 1) of dried form of leaves of *Azadirachta indica*, leaves of *Ocimum sanctum*, fruit of *Prunus amygdalus*, leaves of *Aegle marelose* and fruit of *Vitus vinefera* is particularly preferred. In another embodiment of the present invention, the active ingredients are taken from the any parts of the plants mentioned as above. The ratio of each ingredient is not very critical and 15–40% w/w of one ingredient is taken and is balanced with the ingredients of at least two to all four herbs. The dietary compositions are made with dried plant parts after proper milling to get fine powder and formulated to suitable oral dosage forms.

By using these five different herbs, various compositions (F1–F9) were prepared comprises compositions with 15–40% w/w of all or at least three herbs. The plant ingredients are either in raw form or as medicinal extract of plant parts, and are administered to experimental subjects (both diabetic and normal rats with elevated blood glucose levels and non-insulin dependent diabetic humans) at a dose of 0.01–0.5 gm/Kg body weight. The dosage to be administered is not critical and could be varied depending on status of the disease, diet of the subjects and nature of the subjects (animal or human), age, sex, bodyweight, and physical condition. The dose of dietary compositions made of raw ingredients is little higher than those obtained by extraction procedures, and overdoses of these dietary compositions is not a problem. The extraction methods are known to the person skilled in the art. Generally a subject receives their own dose after some initial dosing to maintain normoglycaemia and then such doses will be continued until some steady states are obtained. The herbal compositions were preferably in suspension form. The herbs were milled to fine powder, mixed and then prepared suspension with distilled water. The powder can be used to prepare different oral dosage forms. Although ingredients of compositions itself has good product stability characteristics, the herbal composition may contain some inert ingredients as required for oral dosage forms. Although, suitable oral dosage forms are formulated and administered, the preferable dosage form is a suspension of the said herbal composition.

The mechanism by which the herbal composition of the invention operates is not exactly understood. However it is assumed that the herbal composition stimulates the pancreas to make its own insulin or assists in some healing mechanism of the diseased pancreatic tissue. The herbs are stimulant to the pancreas and cause the cells of the pancreas to respond and to recommend production of insulin. Since this composition of present invention is holistic in nature and represent in dietary supplements and hence overdosing would not be a problem. And there are no dangers or side effects associated with treatment with this herbal remedy of the invention. The herbal composition also produces beneficial effects such as diuretic, stomachic, antiulcers.

BRIEF DESCRIPTION OF THE ACCOMPANYING DRAWINGS

FIG.-1. Describes the effect of herbal formulation and glibenclamide on oral glucose tolerance tests in rats.

The invention is described in detail herebelow by the following examples which are meant to illustrate the invention and should not be construed as limitations Compositions Various compositions with permutations and combination were tried (Table-1) using *Azadirachta indica, Prunus amygdales, Ocimum sanctum , Aegle marmelos* and *Vitus vinefera*.

TABLE 1

| Composition Code | Azadirachta indica | Prunus amygdales | Ocimum sanctum | Aegle marmelos | Vitus vinefera |
|---|---|---|---|---|---|
| F1 | (20%) | (30%) | (20%) | (15%) | (15%) |
| F2 | (25%) | (30%) | (25%) | (20%) | X |
| F3 | (25%) | (30%) | (25%) | X | (20%) |
| F4 | X | (30%) | (25%) | (25%) | (20%) |
| F5 | (25%) | (30%) | X | (25%) | (20%) |
| F6 | (40%) | (25%) | (35%) | X | X |
| F7 | X | X | (35%) | (35%) | (30%) |
| F8 | (35%) | (40%) | X | X | (25%) |
| F9 | X | (30%) | X | (40%) | (20%) |

EXAMPLE-1

Male albino rats of wistar strains (150–200 g) were used throughout the studies. Rats were divided into eleven groups of each containing 6 rats. These animals were randomly assigned to the following groups which include (A) control group, (B) standard group (glibenclamide, 3 mg/Kg) and (C) test groups (F1–F9). Diabetes was induced by injecting streptozocin (STZ) in a dose of 65 mg/kg intra venous in 0.1M citrate buffer. Rats were kept fasted overnight but were given water ad libitum. After 48 hours of STZ injection, blood samples were taken from tail vein of conscious rats. The blood was centrifuged at 5000 rpm for 10 minutes in an eppendorf tubes containing EDTA (1 mg/ml of blood). Plasma glucose estimations were done by glucose oxidase method by using Auto blood analyzer (Techinicon RA-100, Bayer Diagnostics, Ireland). Animals with blood glucose level more than 250% of the fasting level were considered to be diabetic and were used for the experiment. Group A was given normal saline, group B was given glibenclamide and various groups of C were given herbal compositions for 15 days at least once in day. Blood was collected from tail veins of all the rats after 7 days and 15 days of treatment and glucose levels were estimated as described previously (Table 2). The statistical analysis was performed using Prism program (Graphpad software). ANOVA with post Newman—Keul test with P values was used to compare the treatment efficacy between the test groups.

TABLE 2

Effect of herbal composition on plasma glucose level in experimental rats No. of Rats = 6. P < 0.05

| | | % reduction in glucose levels | |
|---|---|---|---|
| S.N. | Compositions | Day 7 th | Day 15 th |
| 1 | Control | 8 ± 1.4 | 10 ± 2.1 |
| 2 | Glibenclamide | 27 ± 2.6 | 38 ± 2.9 |
| 3 | *F1 | 47 ± 3.9 | 60 ± 6.5 |
| 4 | F2 | 36 ± 3.4 | 45 ± 4.4 |
| 5 | F3 | 33 ± 3.1 | 42 ± 4.6 |
| 6 | F4 | 29 ± 3.1 | 38 ± 3.2 |
| 7 | F5 | 30 ± 3.1 | 40 ± 4.5 |
| 8 | F6 | 25 ± 2.8 | 37 ± 4.1 |
| 9 | F7 | 22 ± 1.9 | 29 ± 3.2 |
| 10 | F8 | 27 ± 3.2 | 31 ± 4.1 |
| 11 | F9 | 24 ± 2.2 | 25 ± 3.1 |

*Significantly higher compared to control group (P < 0.05)

Significant anti-diabetic activity was found in the compositions tested. F1 was found to be most effective out of all the composition tested, which is significantly higher than standard groups, although other groups showed considerable activity.

EXAMPLE-2

Glucose Tolerance Test (GTT)

From the above STZ induced diabetic model the composition 1 has chosen for GTT study.

Male albino rats of wistar strains (150–200 g) were used. They were divided into three groups each containing 6 rats. They were randomly assigned A) control group B) standard group (glibenclamide) C) test group. Group A was given saline, group B was given glibenclamide (3 mg/Kg) and group C was given test compositions. After 2 hours all rats were loaded with glucose with a dose of 5 g/kg. Blood samples were taken from tail vein of conscious rats for every 30 minutes up to 3 hours. Plasma glucose estimations were done by glucose oxidase method by using Auto Blood Analyzer as described in FIG. 1. The statistical analysis was performed using Prism program (Graphpad software). Annova with post Newman—Keul test with P values was used to compare the treatment efficacy between the test groups.

Although activity of the test composition is significantly higher, both composition F1 and glibenclamide showed increased (P<0.05) glucose tolerance compared to control group.

EXAMPLE-3

In this example the composition-1 was tested on humans. Five non-insulin dependent diabetic male patients aged 45–55 years old and an average body weight of 68±5 kg were given composition F1 at a dose of 0.1 gm/Kg for 30 days daily in 3 divided doses, half and hour before breakfast, lunch and dinner. The fasting blood glucose level was monitored for every five days starting from day zero. The results of this test are shown in table-3. Considerable reduction in the blood glucose levels were observed in all the individuals although the response varied significantly. It is concluded that some changes in dosage regime and diet would give a proper control of diabetes in non-insulin dependent diabetic patients. It is assumed that, these herbal compositions could be used in type I diabetic patients along with insulin therapy as ingredients of this compositions could increased peripheral insulin sensitivity, and hence insulin dose could be reduced.

TABLE 3

Effect of herbal composition on blood glucose level in humans

| Patient No. | Day zero | Day five | Day ten | Day fifteen | Day twenty | Day twenty five | Day thirty |
|---|---|---|---|---|---|---|---|
| 1 | 170 | 164 | 153 | 146 | 141 | 135 | 124 |
| 2 | 145 | 132 | 129 | 126 | 112 | 105 | 102 |
| 3 | 163 | 161 | 155 | 139 | 135 | 140 | 141 |
| 4 | 147 | 145 | 133 | 131 | 126 | 109 | 119 |
| 5 | 153 | 154 | 141 | 136 | 128 | 113 | 99 |

What is claimed is:

1. An edible therapeutic herbal composition useful as a hypoglycemic agent, said composition comprising herbs *Prunus amygdalus* of concentration of about 30% w/w, *Ocimum sanctum* of concentration of about 20% w/w, *Azadirachta indica* of concentration of about 20% ww, *Aegle marelose* of concentration of about 15% w/w, and *Vitus vinefera* of concentration of about 15% ww.

2. A composition as described in claim 1 wherein the composition is formulated as oral dosage forms comprising solutions, suspensions, emulsions, gels, pastes, elixirs, viscous colloidal dispersions, tablets, capsules and/or oral control release types or such delivery forms suitable for oral route.

3. A composition as claimed in claim 1, wherein the herbs are selected from dried fruits of *Prunus amygdalus,* leaves of *Ocimum sanctum,* leaves of *Azadirachta indica,* leaves of *Aegle marelose,* and fruits of *Vitus vinefera.*

4. A method of treatment for hyperglycemia in an animal, comprising the step of oral administration of the herbal composition of claim 1 to the animal in a therapeutically effective amount.

5. A method as claimed in claim 4 wherein the herbal composition is administered before the animal eats food.

6. A method as claimed in claim 4 wherein the herbal composition is administered to the animal in food.

7. A method as claimed in claim 4, wherein the composition is administered in a dosage form containing 0.01–0.5 gm/Kg. of the composition.

8. A method for reducing the blood glucose level in a mammal which comprises administering a therapeutically effective amount of the composition of claim 1 to the mammal.

9. A method as claimed in claim 4, wherein the animal is a human.

* * * * *